US 11,904,147 B2

(12) United States Patent
Wegener et al.

(10) Patent No.: US 11,904,147 B2
(45) Date of Patent: Feb. 20, 2024

(54) METHODS AND SYSTEMS FOR MATING DISPOSABLE SYRINGES WITH PNEUMATIC DRIVERS WITHOUT BREAKING STERILITY

(71) Applicant: Fenwal, Inc., Lake Zurich, IL (US)

(72) Inventors: Christopher J. Wegener, Libertyville, IL (US); Alexandra Salomon, Chicago, IL (US); Bret M. Olson, Chicago, IL (US); Keith Grider, Chicago, IL (US); Tom Matusaitis, Chicago, IL (US)

(73) Assignee: Fenwal, Inc., Lake Zurich, IL (US)

( * ) Notice: Subject to any disclaimer, the term of this patent is extended or adjusted under 35 U.S.C. 154(b) by 950 days.

(21) Appl. No.: 16/701,591

(22) Filed: Dec. 3, 2019

(65) Prior Publication Data
US 2020/0197942 A1 Jun. 25, 2020

Related U.S. Application Data (60) Provisional application No. 62/815,106, filed on Mar. 7, 2019, provisional application No. 62/781,955, filed on Dec. 19, 2018.

(51) Int. Cl.
*B01L 9/00* (2006.01)
*A61M 5/315* (2006.01)
(Continued)

(52) U.S. Cl.
CPC ............ *A61M 5/31578* (2013.01); *A61J 1/05* (2013.01); *A61M 1/362265* (2022.05);
(Continued)

(58) Field of Classification Search
CPC ............ A61M 5/31578; A61M 5/3145; A61M 1/0281; A61M 1/3692; A61M 2005/3109;
(Continued)

(56) References Cited

U.S. PATENT DOCUMENTS 5,452,824 A * 9/1995 Danek ................ B05C 11/1034
222/327
6,715,506 B1 4/2004 Ikushima
(Continued)

FOREIGN PATENT DOCUMENTS

CN 107367432 A * 11/2017 ............... G01N 3/36
EP 1089782 B1 10/2002
(Continued)

OTHER PUBLICATIONS

European Patent Office, Extended European Search Report, counterpart European Appl. No. EP19216478, (dated May 18, 2020), (7 pages).

(Continued)

*Primary Examiner* — Matthew D Krcha
*Assistant Examiner* — Sophia Y Lyle
(74) *Attorney, Agent, or Firm* — Cook Alex Ltd.

(57) ABSTRACT

A pneumatic driver for a syringe is provided. The syringe has an elongated barrel with a cap secured to the proximal end that has a through bore. A filter is secured to the cap interior of the barrel that covers an opening in the through bore interior of the barrel. The pneumatic driver includes a source of pressurized air; a support for receiving and locating the syringe; and a supply block configured to receive pressurized air from the source and having an outlet for delivery of pressurized air. The supply block is movable between a first position spaced apart from the cap of the syringe and a second position in contact with the cap with fluid communication being established between the outlet of the supply block and the through-bore in the cap.

16 Claims, 10 Drawing Sheets (51) Int. Cl.
  *A61M 5/31* (2006.01)
  *G05D 7/06* (2006.01)
  *A61J 1/05* (2006.01)
  *B65D 51/16* (2006.01)
  *A61M 1/36* (2006.01)
  *A61M 1/02* (2006.01)

(52) U.S. Cl.
  CPC ............. *A61M 5/3145* (2013.01); *B01L 9/00* (2013.01); *B65D 51/1616* (2013.01); *G05D 7/0623* (2013.01); *A61M 1/0281* (2013.01); *A61M 1/3692* (2014.02); *A61M 2005/3109* (2013.01); *A61M 2205/273* (2013.01); *B01L 2300/042* (2013.01); *B01L 2300/06* (2013.01); *B01L 2300/0609* (2013.01); *B01L 2300/0627* (2013.01)

(58) Field of Classification Search
  CPC .......... A61M 2205/273; A61M 5/2053; A61M 2005/2026; A61M 5/281; A61M 5/14526; A61M 5/178; A61M 5/20; A61J 1/05; B01L 9/00; B01L 2300/042; B01L 2300/06; B01L 2300/0609; B01L 2300/0627; B65D 51/1616; G05D 7/0623
  See application file for complete search history.

(56) References Cited

U.S. PATENT DOCUMENTS

| | | |
|---|---|---|
| 6,966,894 B1 | 11/2005 | Urich |
| 7,195,610 B1 | 3/2007 | Flachbart |
| 8,647,305 B2 | 2/2014 | Ohta et al. |
| 8,690,828 B2 | 4/2014 | Fujioka et al. |
| 9,309,042 B2 | 4/2016 | Digregorio et al. |
| 9,346,075 B2 | 5/2016 | Aguilar et al. |
| 9,393,370 B2 | 7/2016 | Auld et al. |
| 9,808,825 B2 | 11/2017 | Aguilar et al. |
| 9,808,826 B2 | 11/2017 | Aguilar et al. |
| 9,958,067 B2 | 5/2018 | Strong et al. |
| 10,029,052 B2 | 7/2018 | Auld et al. |
| 10,300,505 B2 | 5/2019 | Aguilar et al. |
| 10,441,967 B2 | 10/2019 | Ikushima |
| 10,668,247 B2 | 6/2020 | Anand et al. |
| 10,675,438 B2 | 6/2020 | Anand et al. |
| 10,926,895 B2 | 2/2021 | Wegener et al. |
| 2004/0122367 A1 | 6/2004 | Sculati |
| 2006/0100590 A1 | 5/2006 | Thorne, Jr. et al. |
| 2008/0281265 A1 | 11/2008 | Hochman |
| 2009/0124996 A1 | 5/2009 | Heneveld et al. |
| 2009/0198183 A1 | 8/2009 | Krumme et al. |
| 2011/0224612 A1 | 9/2011 | Lum et al. |
| 2013/0092630 A1 | 4/2013 | Wegener |
| 2013/0341291 A1 | 12/2013 | Wegener et al. |
| 2014/0052078 A1* | 2/2014 | Heinz ................... A61M 5/347 604/241 |
| 2014/0199680 A1 | 7/2014 | Min et al. |
| 2014/0367409 A1 | 12/2014 | Digregorio et al. |
| 2016/0175530 A1* | 6/2016 | Mide ..................... A61M 5/347 604/535 |
| 2017/0204371 A1 | 7/2017 | Wegener |
| 2018/0093040 A1 | 4/2018 | Thorne, Jr. et al. |
| 2018/0155070 A1 | 6/2018 | Min et al. |
| 2020/0009312 A1 | 1/2020 | Min et al. |
| 2020/0046899 A1 | 2/2020 | Cane' |
| 2020/0197620 A1 | 6/2020 | Brown |
| 2020/0297966 A1 | 9/2020 | Anand et al. |

FOREIGN PATENT DOCUMENTS

| | | |
|---|---|---|
| EP | 1208858 B1 | 6/2006 |
| EP | 2032467 B1 | 8/2010 |
| EP | 2223868 B1 | 2/2012 |
| EP | 2561932 A2 | 2/2013 |
| EP | 1155748 B1 | 4/2017 |
| EP | 2854727 B1 | 4/2019 |
| EP | 3 569 266 A1 | 11/2019 |
| EP | 3175928 B1 | 1/2020 |
| EP | 3590556 A1 | 1/2020 |
| EP | 3669907 A1 | 6/2020 |
| EP | 3669908 A1 | 6/2020 |
| EP | 3669910 A1 | 6/2020 |
| JP | 2010125405 A | 6/2010 |
| WO | WO200012158 A1 | 3/2000 |
| WO | WO200040346 A1 | 7/2000 |
| WO | WO2007055697 A1 | 5/2007 |
| WO | WO2007146921 A2 | 12/2007 |
| WO | WO2010119622 A1 | 10/2010 |
| WO | WO2011010467 A1 | 1/2011 |
| WO | WO2013177215 A1 | 11/2013 |
| WO | WO2016017453 A1 | 2/2016 |
| WO | WO2018065880 A1 | 4/2018 |
| WO | WO2019099583 A1 | 5/2019 |
| WO | WO2019099740 A1 | 5/2019 |

OTHER PUBLICATIONS

Office Actions dated Jul. 6, 2022 and Nov. 25, 2022 for co-pending U.S. Appl. No. 16/701,742, having same claim of priority.

* cited by examiner

METHODS AND SYSTEMS FOR MATING DISPOSABLE SYRINGES WITH PNEUMATIC DRIVERS WITHOUT BREAKING STERILITY

TECHNICAL FIELD

The present disclosure is directed broadly to systems and methods for washing suspensions of biological cells. More particularly, the present disclosure is directed to systems and methods for washing small volumes of biological cells utilizing syringes actuated by pneumatic drivers for effecting movement of fluid through the system.

BACKGROUND

A number of well-known therapies are currently practiced in which a targeted cellular blood component (e.g., red blood cells, white blood cells, and platelets) is separated from whole blood and stored for later infusion to a patient. The targeted cellular product (e.g., red blood cells or platelets) may be in a suspension that includes plasma and/or some other supernatant. As such, it is sometimes desirable to "wash" the cellular suspension (typically with saline) to remove the plasma/supernatant, as well as any non-target cellular material, prior to reinfusion.

Systems and methods for cell washing are exemplified by US 2013/0341291, US 2013/0092630, and US 2014/0199680, each of which is incorporated herein by reference. Each of these published applications discloses cell washing methods utilizing systems and fluid circuits including a spinning membrane separator. Such systems include peristaltic pumps and pinch valves that act on tubing to direct flow within the fluid circuit.

The fluid circuits in the cited published applications have a relatively large internal volume, and thus require relatively large volumes of wash or flush media to clear processed fluid through the fluid circuit. While such systems and fluid circuits are capable of washing and reducing the volume of the targeted cellular component into final volumes of ranging from approximately 50 mL to 5,000 mL, there are instances in which smaller final volumes (e.g., 10 mL) are desired, such as when processing single-dose quantities of mononuclear cell products. A system and method for washing small volumes of cells is shown in US 2017/0204371, which is incorporated herein by reference.

More specifically, US 2017/0204371 discloses a fluid circuit for cell washing that comprises a spinning membrane separator and a fluid management system comprising a cassette. The cassette defines the fluid pathways, and includes internally mechanical valving, pressure sensing and air sensing for controlling flow through the fluid pathways. Additionally, the fluid circuit comprises syringes that are acted on by syringe pumps or drivers that are associated with the hardware component of the system to move the stoppers of the syringes within the syringe barrel, and thus provide pressure for moving fluid through the circuit.

US 2018/0155070, which is also incorporated by reference herein, discloses a variety of options for filling a cell product into a container, including end user containers, in which the container may take the form of a syringe. A vacuum/pressure source is associated with the syringe to move the plunger head assembly within the barrel of the syringe. Positional sensors provide signals indicative of the location of the stopper within the syringe barrel During various stages of a washing procedure, such as that contemplated by US 2017/0204371, and a fill procedure, such as that contemplated by US 2018/0155070, suspensions of biological cells, supernatant and the like are drawn into and discharged from the barrels of the syringes. Thus, it is important to maintain the sterility of the syringes, while at the same time providing for efficient and controlled movement of the cell suspension through the system.

By way of the present application, a syringe and a pneumatic syringe driver are provided in which the pneumatic driver includes structure that locates and supports the syringe, and sealingly engages the syringe so that the stopper of the syringe can be driven without breaking sterility and opening the system.

SUMMARY

An actuator or driver for a syringe is provided in which the syringe comprises an elongated barrel having a first end, with a cap secured to the first end having a through-bore. In a first aspect, the actuator comprises a source of pressurized air; supports for receiving and locating the syringe; and a supply block configured to receive pressurized air (both positive and negative/vacuum) from the source and having an outlet for delivery of pressurized air. The supply block is movable between a first position spaced apart from the cap of the syringe and a second position in contact with the cap, with fluid communication being established between the outlet of the supply block and the through-bore in the cap.

In a second aspect, a seal is associated with one of the outlet of the supply block and the through-bore in the cap to provide a seal therebetween when the supply block is in the second position.

In a third aspect, the actuator further comprises a base, with the source of pressurized air, the supports for receiving the syringe, and the supply block being mounted to the base.

In a fourth aspect, the source of pressurized air and the support for receiving the syringe are affixed to the base. The supply block is movably attached relative to the base for movement between the first and second positions by a plurality of links, each link having a first and second end, the first end of each link being pivotally secured to the base and the second end of each link being pivotally secured to the supply block.

In a fifth aspect, the actuator further comprises a lever pivotally attached relative to the base and one or more further links having first and second ends, the first end of the further link being pivotally secured to the lever and the second end of the further link being pivotally secured to the supply block, such that movement of the lever relative to the base moves the supply block between the first and second positions.

In a sixth aspect, the lever further comprises a cover, the cover being spaced from the base when the supply block is in the first position and adjacent to the base when the supply block is in the second position.

In a seventh aspect, the plurality of links comprises two pairs of links pivotally securing the supply block relative to the base, so that the links of each pair are substantially parallel throughout a range of motion from the first position to the second position.

In an eighth aspect, the actuator further comprises a first permanent magnet secured to the base and a second permanent magnet secured to the supply block, such that the first and second magnets are in proximity when the supply block is in the first position with a sufficient force of attraction to maintain the supply block in the first position in the absence of a further external force being applied to the supply block.

In a ninth aspect, the actuator further comprises an air flow pathway from the source of pressurized air to the supply block, one or more valves for controlling air flow through the air flow pathway, one or more pressure sensors for measuring air pressure within the air flow pathway and providing a signal indicative of the air pressure, and a programmable controller programmed to automatically control air flow through the air flow pathway by actuation of the one or more valves in response to signals received from the one or more pressure sensors, sensors providing positional feedback for the stopper, time limits, or other programmed behaviors.

In a tenth aspect, the supply block defines a longitudinal axis generally aligned a longitudinal axis of a syringe received in the support, and the actuator further comprises a latch pivotally mounted relative to the base comprising an arcuate track, and a guide block secured to the base comprising a linear track generally aligned with the longitudinal axis of the supply block. The supply block further comprises a follower received in both the arcuate track of the latch and the linear track of the guide block, such that, when the latch is pivoted, the arcuate track engages the follower to move the follower along the linear track and to thus move the supply block between the first and second positions.

In an eleventh aspect, the outlet of the supply block comprises a luer fitting.

In a twelfth aspect, the luer fitting is threaded and the supply block is rotatable.

DETAILED DESCRIPTION

A more detailed description of the systems and methods in accordance with the present disclosure is set forth below. It should be understood that the description below of specific devices and methods is intended to be exemplary, and not exhaustive of all possible variations or applications. Thus, the scope of the disclosure is not intended to be limiting, and should be understood to encompass variations or embodiments that would occur to persons of ordinary skill.

Turning to the drawings, a pneumatic syringe driver or actuator 10 is shown which may be used in combination with a disposable syringe 12. As is typical of a standard syringe, the syringe generally comprises an elongated barrel 14 having a first or proximal end and a second or distal end. The barrel is open on the first end and terminates in a hollow tip on the second end. The tip of the syringe may further be configured to comprise a luer lock 16.

Figure 15:
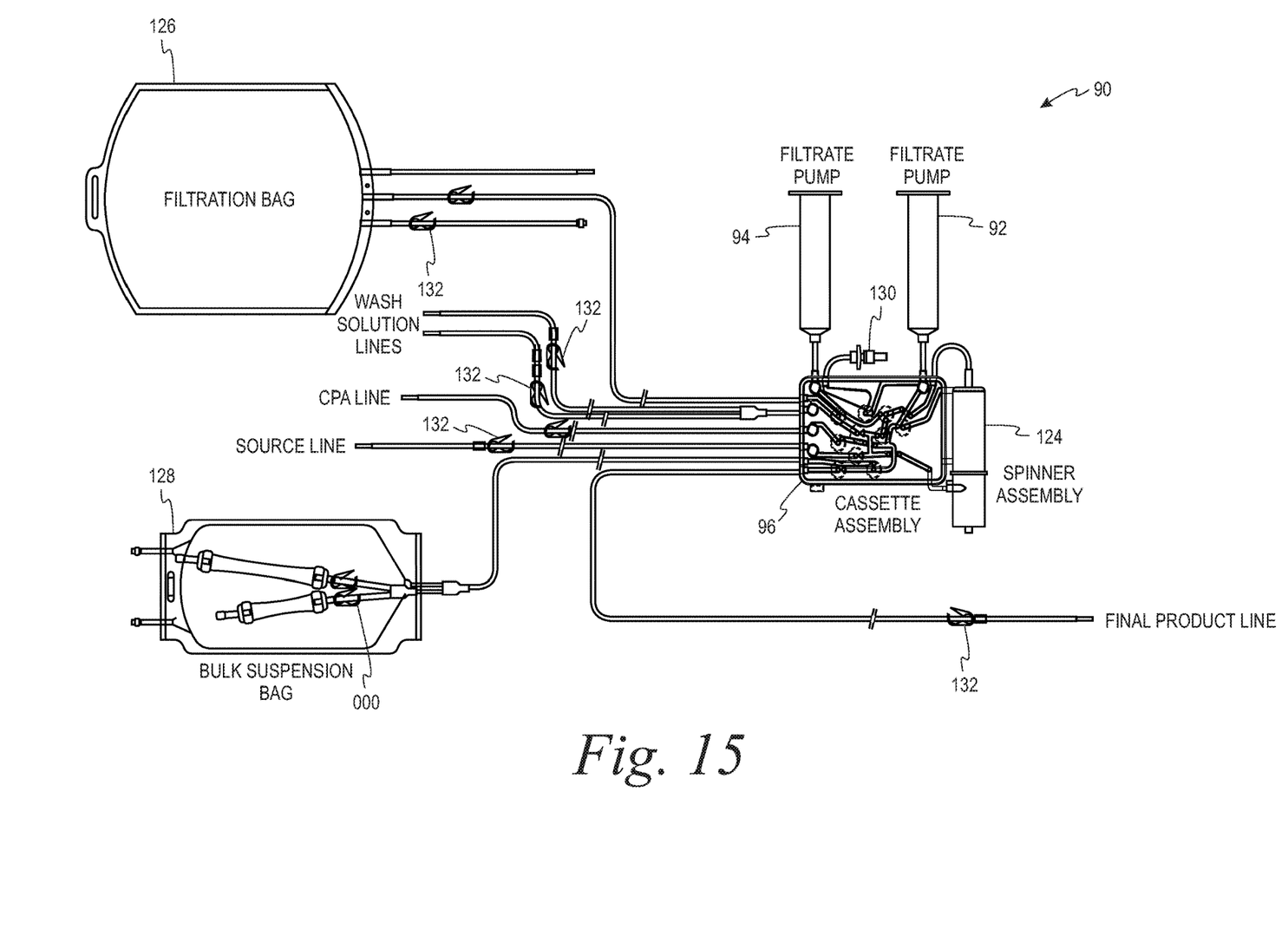
FIG. 15 is a schematic view of a disposable processing set that includes elongated syringe barrels of the type that would be used with the pneumatic driver of the present disclosure.

The elongated barrel 14 of the syringe is preferably incorporated into a disposable processing set. A representative processing set 90 is shown in FIG. 15. With reference to FIG. 15, the disposable processing set 90 includes two elongated syringe barrels 92, 94, with elongated barrel 92 for the syringe that provides the motive force for the retentate, and the elongated barrel 94 for the syringe that provides the motive force for the filtrate.

Figure 16:
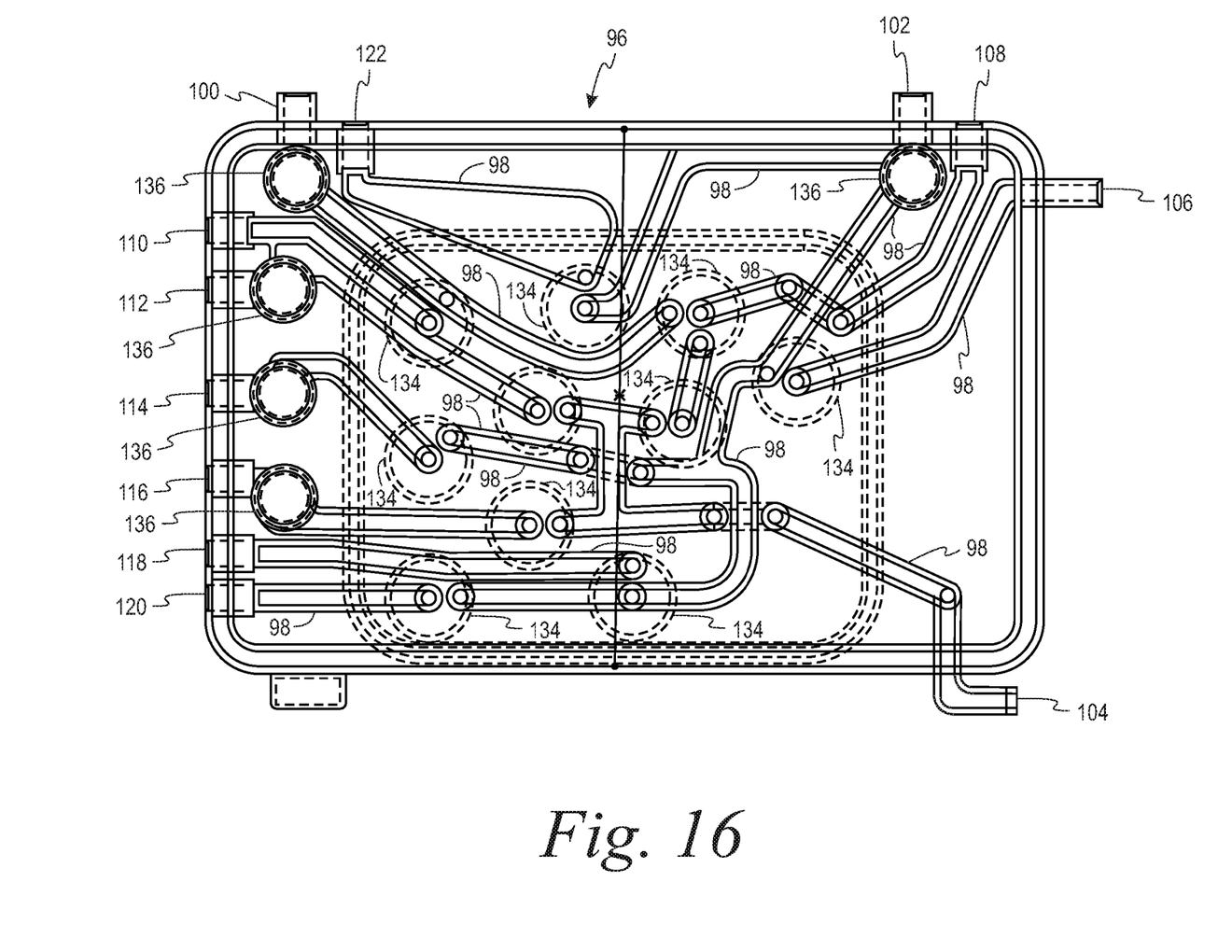
FIG. 16 is an enlarged view of a flow control cassette forming part of the disposable processing set of FIG. 15.

The disposable processing set 90 also includes a flow control cassette 96, best seen in FIG. 16. The flow control cassette 96 has a plurality of passageways 98 defined on the interior thereof that are in fluid communication with various of a plurality of ports 100, 102, 104, 106, 108, 110, 112, 114, 116, 118, 120, 122 on the exterior wall of the cassette 96. The outlets of the elongated syringe barrels 92, 94 are respectively connected by a tubing segment to ports 100, 102. Ports 104, 106 and 108 respectively connect the inlet, the retentate outlet and the filtrate outlet of a spinning membrane separator 124 to the cassette. Port 110 connects to a tubing segment associated with a container/bag 126 for receiving filtrate; port 112 connects to a tubing segment associated with one or more containers (not shown) of wash solution; port 114 connects to a tubing segment associated with a container (not shown) of an alternate solution depending on the application (e.g., the solution could be a cryopreservation solution); port 116 connects to a tubing segment associated with a source container (not shown); port 118 connects to a tubing segment associated with a bulk suspension bag 128; port 120 connects to a tubing segment associated with a final product container (not shown); and port 122 connects to a tubing segment associated with a vent 130. Various of the tubing segments are provided with manual pinch clamps 132, such as Roberts' clamps.

Fluid flow through the cassette 96 is controlled by a series of valves 134 that are opened and closed to selectively interconnect the passageways 98. In addition, air detectors 136 associated with ports 100, 102, 112, 114, and 116 of the cassette provide signals to a programmable controller that automatically opens and closes the valves to direct fluid through passageways and ports of the cassette.

The pneumatic driver 10 includes an air supply block 18 that sealingly engages the syringe 12 to introduce positive or negative air pressure into the barrel 14 of the syringe. The positive and negative air pressure serve to repeatedly move the stopper 20 of the syringe axially back and forth within the barrel 14 to draw fluid into the syringe (with the application of negative air pressure or a vacuum force) or to expel fluid from the barrel of the syringe (with the application of positive air pressure).

The proximal end of the syringe barrel is provided with a cap 22 having a through bore 24, through which pressurized air is introduced into the barrel of the syringe by means of the air supply block 18. Preferably, the cap 22 is removably secured to the barrel 14 to permit post-use examination of the cap 22, as described in greater detail below.

Figure 11:
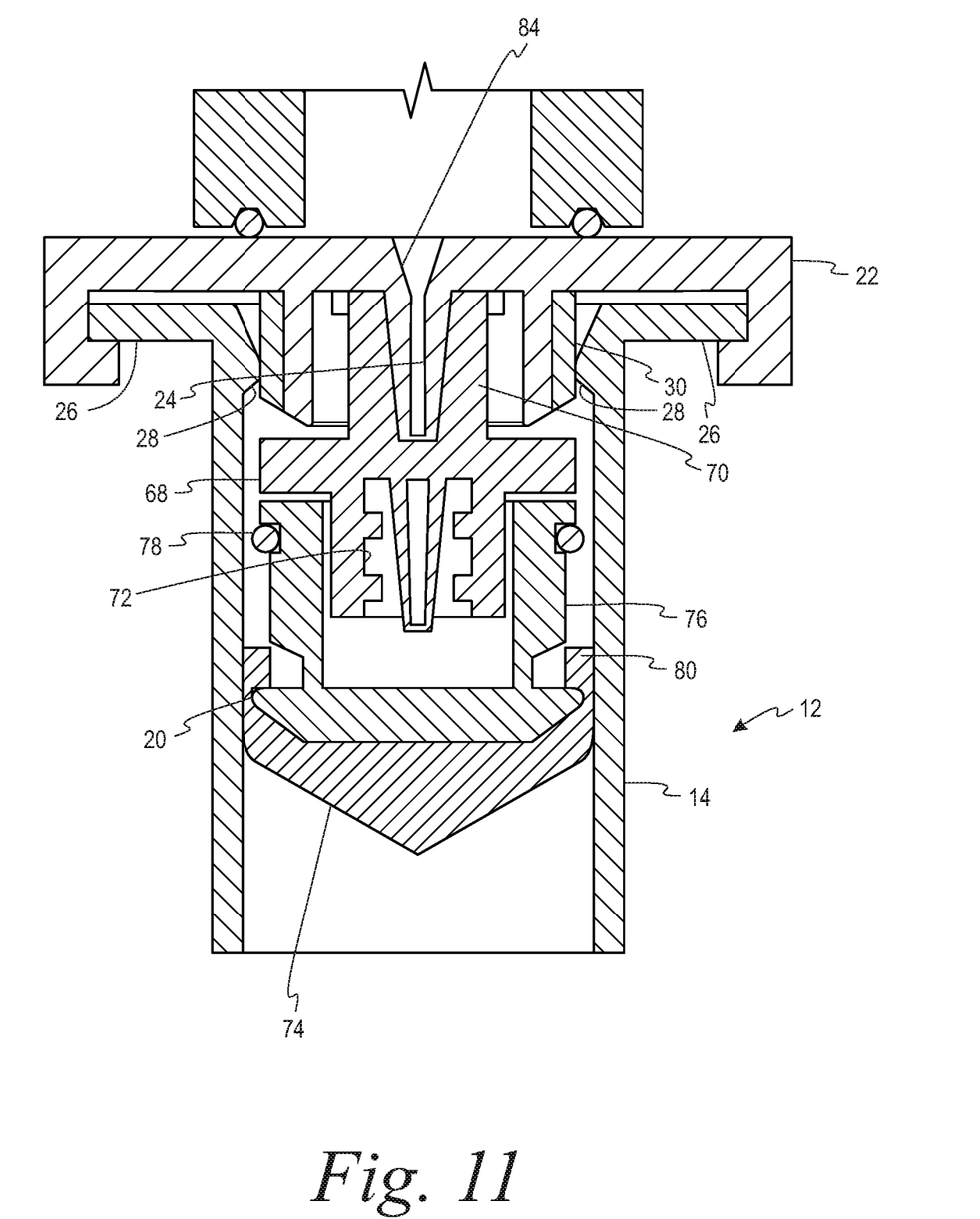
FIG. 11 is an enlarged fragmentary cross sectional view of the upper or proximal end of a disposable syringe in accordance with the present application.

As illustrated, the barrel 14 of the syringe further comprises a collar or flanges 26 at the first end that extend laterally from the barrel (which typically provide a surface for grasping the syringe with the index finger and middle finger), and the cap 22 is mounted to the flanges 26. Further, as illustrated, the barrel 14 of the syringe is formed with an annular, inwardly-projecting ridge 28 adjacent the proximal end for sealingly engaging an annular, radially-projecting seal or gasket 30 associated with the cap 22 (as best seen in FIG. 11). However, alternate sealing configurations are contemplated.

Figure 7:
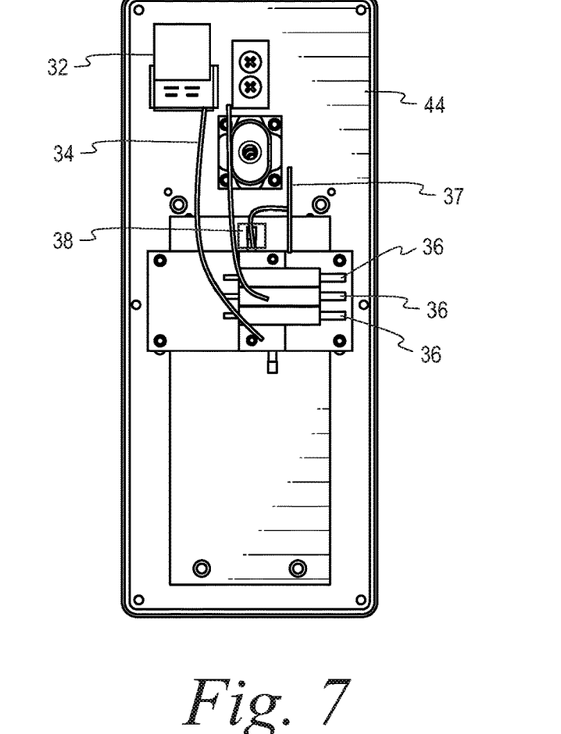
FIG. 7 is a rear view of the pneumatic driver.
Figure 8:
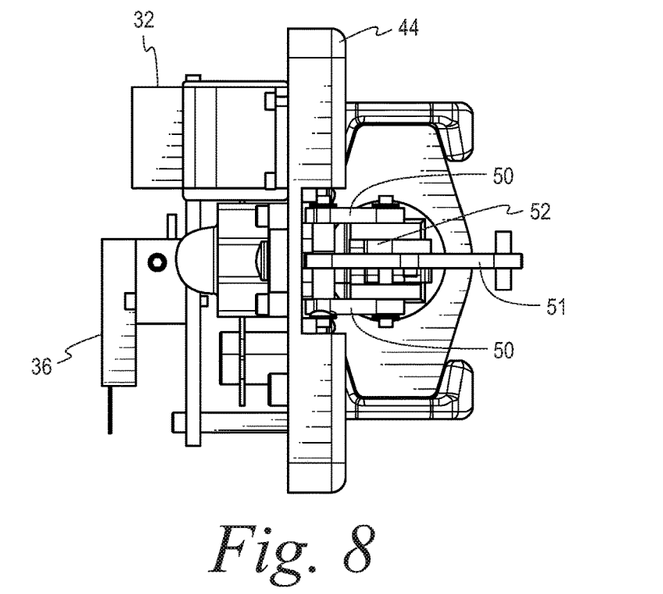
FIG. 8 is a top view of the pneumatic driver, with the cover removed for clarity.
Figure 9:
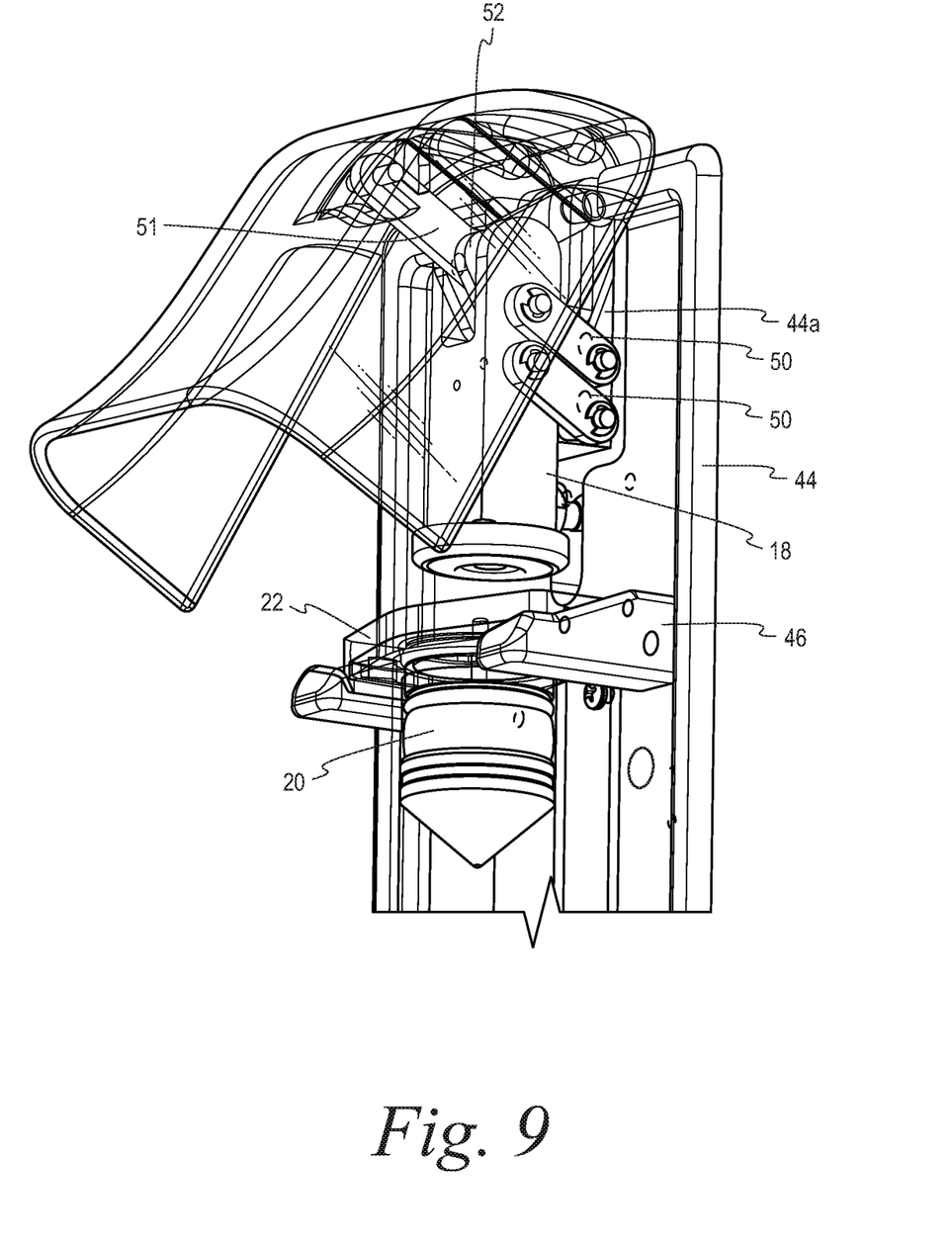
FIG. 9 is an enlarged fragmentary perspective view of the pneumatic driver in combination with a disposable syringe, with the pneumatic driver in the open position.

Generally speaking, the pneumatic driver or actuator 10 comprises a source of pressurized air 32. As illustrated, the pneumatic source 32 comprises a compressor pump, but could alternatively comprise pressure and vacuum reservoirs or, possibly, a syringe or hand pump. The air supply block 18 is configured to receive pressurized air from the pneumatic source 32 by means of a first set of tubes 34 that connect the pneumatic source 32 to a series of valves 36, and a second set of tubes 37 that connect the valves 36 to a pressure sensor 38 (best seen in FIG. 7) and to the air supply block 18. A programmable controller 39 is preferably provided to automatically control air flow through the air flow pathway by turning the pneumatic source on and off and actuation of the valves 36 in response to signals received from the pressure sensor 38, and or from sensors providing positional feedback for the stopper (e.g., as described in US 2018/0155070), time limits, or other programmed behaviors.

Figure 1:
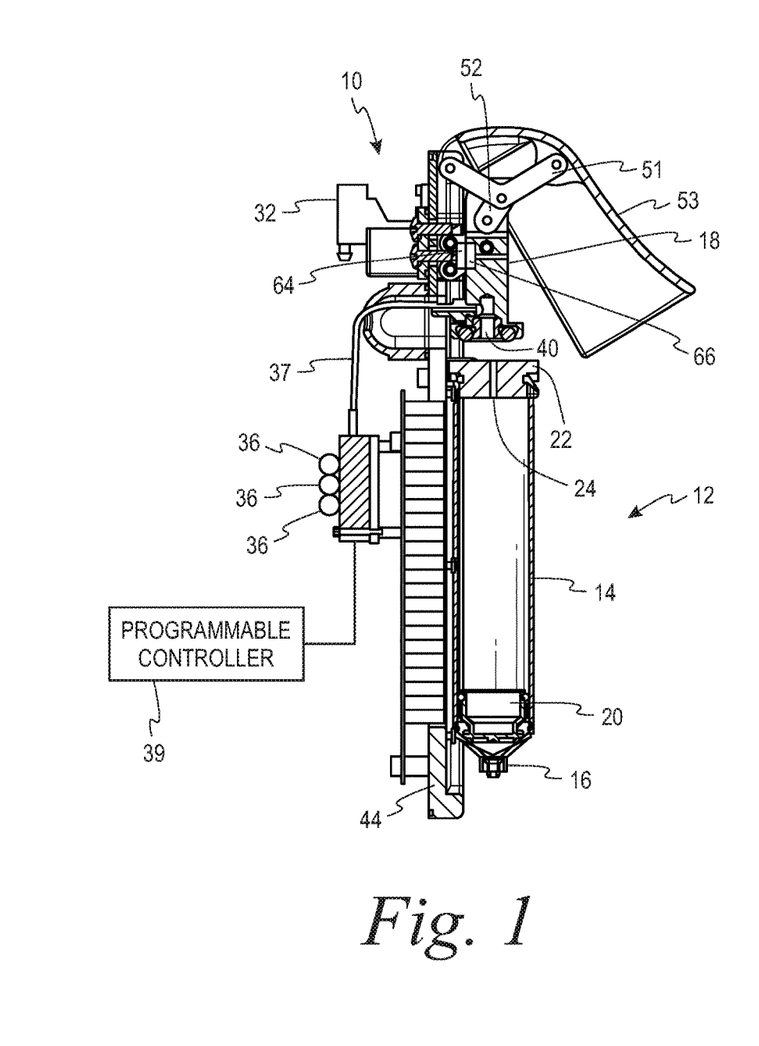
FIG. 1 is a side view, in partial cross section, of a pneumatic driver in combination with a disposable syringe, with the pneumatic driver in the open position, in accordance with the present application.
Figure 2:
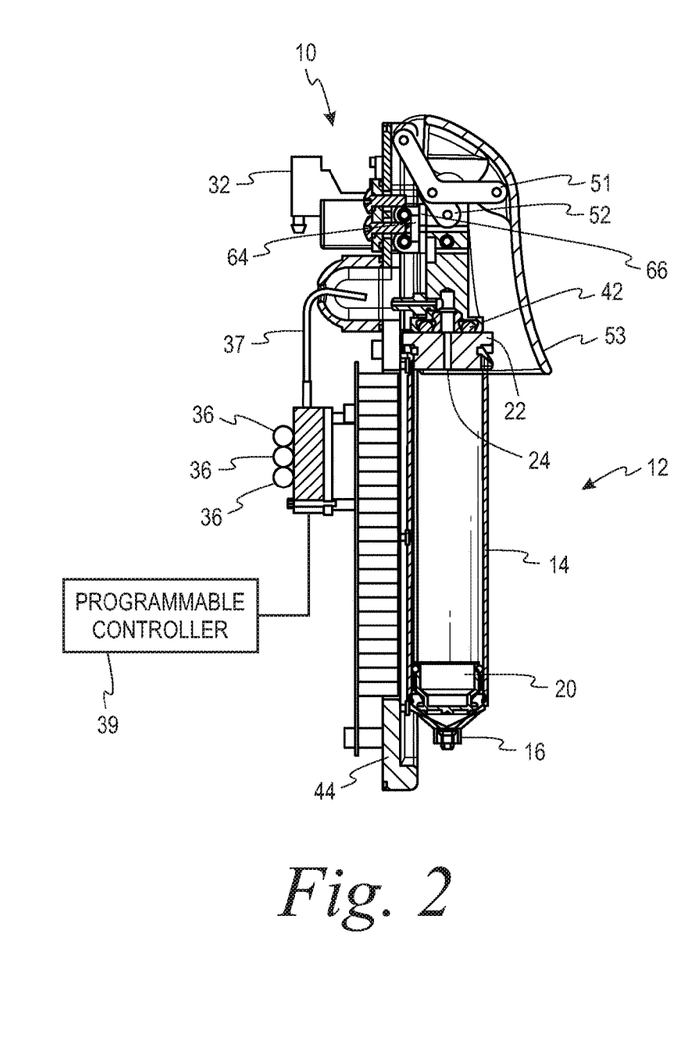
FIG. 2 is a side view, in partial cross section, of the pneumatic driver in combination with a disposable syringe, with the pneumatic driver in the closed position.
Figure 3:
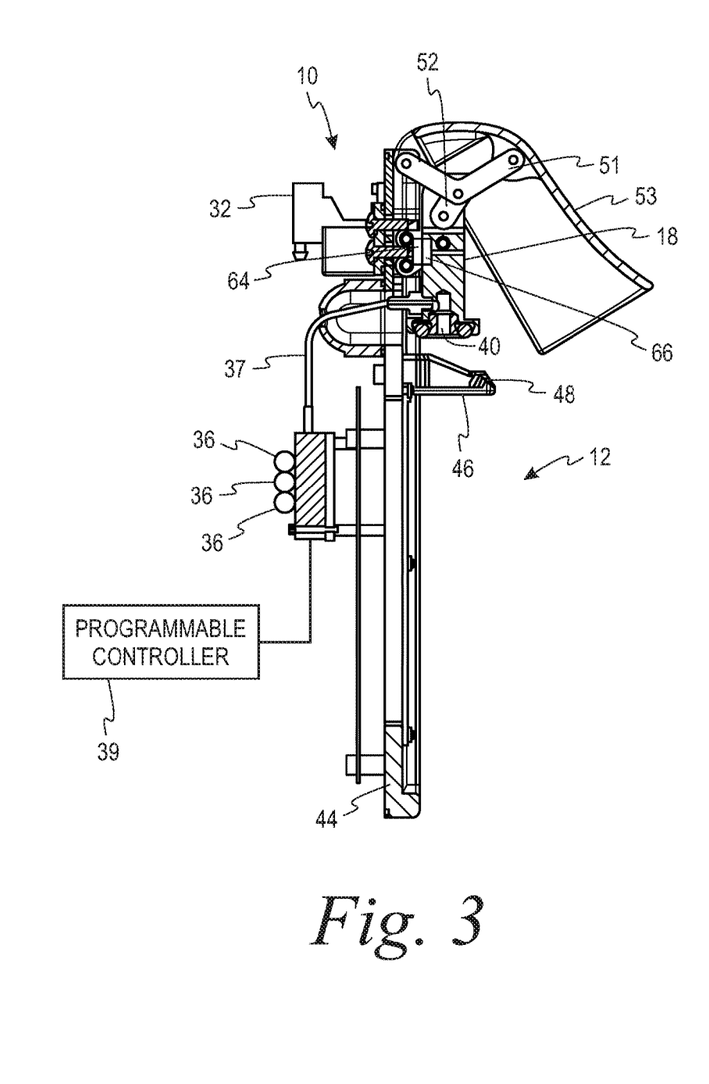
FIG. 3 is a side view, in partial cross section, of the pneumatic driver, with the pneumatic driver in the open position.
Figure 4:
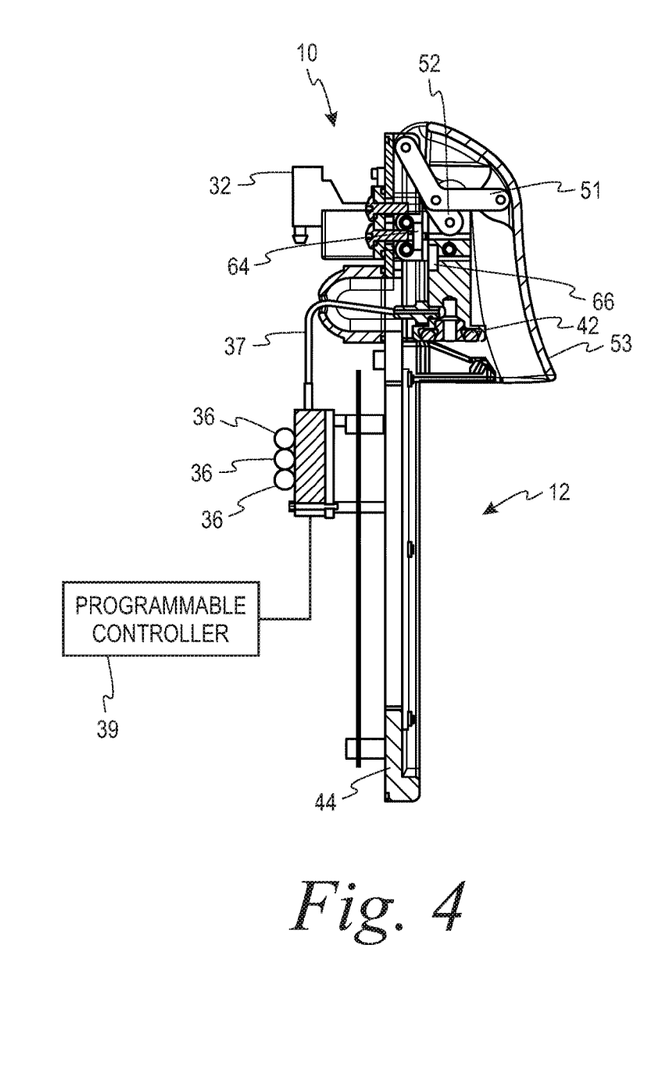
FIG. 4 is a side view, in partial cross section, of the pneumatic driver, with the pneumatic driver in the closed position.
Figure 5:
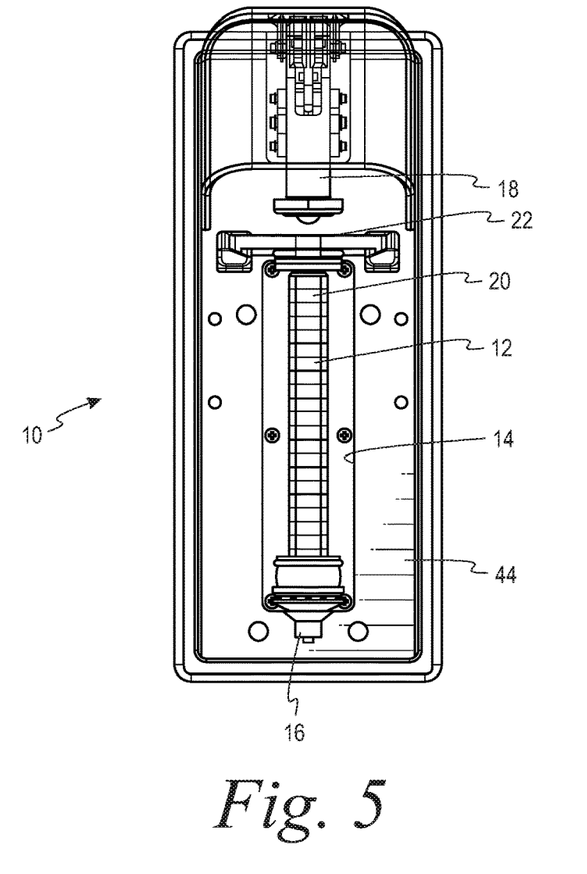
FIG. 5 is a front view of the pneumatic driver in combination with a disposable syringe, with the pneumatic driver in the closed position.
Figure 6:
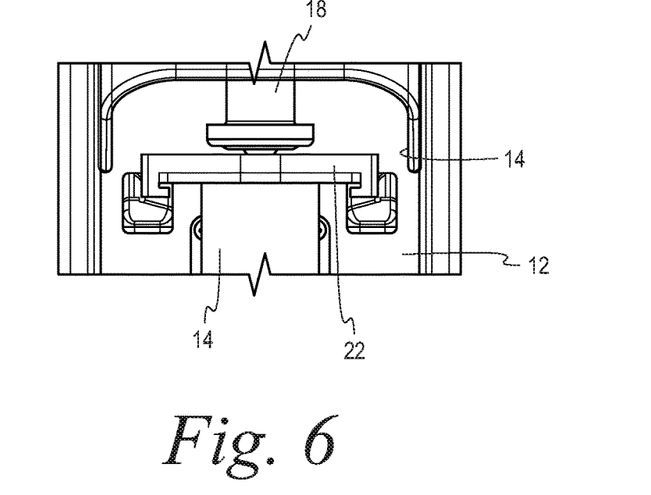
FIG. 6 is an enlarged fragmentary front view of the pneumatic driver in combination with a disposable syringe, with the pneumatic driver in the closed position.

The supply block 18 includes an outlet 40 for the delivery of pressurized air to the barrel 14 of the syringe 12 through the through bore 24 in the cap 22. To this end, the air supply block 18 is movable between a first position spaced apart from the cap 22 of the syringe (FIG. 1) and a second position in contact with the cap (FIG. 2), with fluid communication being established between the outlet 40 of the supply block 18 and the through bore 24 in the cap 22.

A seal 42 is provided between the outlet 40 of the air supply block 18 and the through-bore 24 in the cap 22 when the air supply block 18 is in the second position. Preferably, the seal 42 comprises a resilient O-ring or other compliant gasket captured in the face of the air supply block. Alternatively, the top face of the cap 18 of the syringe could include an O-ring seal or gasket that surrounds the inlet of the through bore 20. The cavity defined by the O-ring or gasket 42 is larger than the inlet in the through bore 24, thus accommodating some misalignment between the outlet of the air supply block and the inlet of the through bore. The O-ring or gasket 42 also serves to provide some tactile feedback as the air supply block 18 is brought into engagement with the cap 22, and further accommodates some planar misalignment between the mating surfaces of the air supply block and the cap. Alternatively, the outlet 40 of the air supply block 18 may comprises a luer fitting for mating with a complementary luer fitting formed by the inlet of the through bore 24 in the cap 22. Further, the luer fittings may be threaded and the supply block configured to be rotatable for coupling the luer fitting of the air supply block with that of the cap.

As illustrated, the pneumatic actuator also comprises a base 44, to which are mounted the source of pressurized air 32 and the air supply block 18. Also mounted to the base 44 is a support 46 that cooperates with the cap 22 of the syringe 12 to mount the syringe 12 to the actuator 10, with the air supply block 18 defining a longitudinal axis generally aligned with the longitudinal axis of a syringe 10 received in the support 46 when the air supply block is in the closed position. Preferably, the support 46 comprises a pair of arms that are spaced apart a distance sufficient to receive the barrel 14 of the syringe therebetween. The front or outer edges of the arms including a raised edge or shoulder 48 which serves to positively locate the cap 22 in the support 46.

The air supply block 18 is movably attached to the base 44 for movement between a first "open" position (to permit a syringe 12 to be loaded onto or removed from the support 46), and second "closed" position (in which the air supply block 18 is brought into sealing engagement with the cap 22 of the syringe 14). To this end, the air supply block 18 is mounted to the base 44 by a plurality of links 50, each link 50 having a first and second end. The first end of each link is pivotally secured to an adapter plate 44a that is secured to the base 44 in a manner to permit the location of the adapter plate 44a relative to the base 44 to be adjusted. For example, the base 44 may include slots for receiving threaded bolts that secure the adapter plate 44a to the base so that the adapter plate may be moved relative to the base 44 along the slots. The second end of each link is pivotally secured to the air supply block 18.

As illustrated, two pairs of links 50 are pivotally secured to the air supply block 18 and the adapter plate 44a, so that the links 50 of each pair are substantially parallel throughout a range of motion from the first position to the second position. Such a four link assemblage is commonly referred to as a "four-bar linkage." The tolerances of the four bar linkage assembly may be sufficiently loose to allow for any planar misalignment between the air supply block 18 and the cap 22, while still holding the syringe 12 securely. However, the tolerances should not be so loose as to permit the user to feel the looseness.

A lever 51 is provided for moving the air supply block 18 between the open and closed positions. The lever 51 is pivotally attached to the adapter plate 44a. A pair of further links 52 are provided, each link 52 having first and second ends, with the first end of each link 52 being pivotally secured to the lever 51 and the second end of the link 52 being pivotally secured to the air supply block 18.

Movement of the lever 51 relative to the base 44 moves the air supply block 18 between the first, open position and the second closed position. Preferably, when in the second, closed position, links 52 go over center to abut the adapter plate 44a to act as a stop. Thus, the lever 51 and links 52 form an over-center latching mechanism. Consequently, a vertically upward force on the syringe 12 does not move the air supply block 18, while an upward force applied directly to the lever 51 will cause the links 52 to move the air supply block to the open position. As illustrated, the lever 51 is intended to be manually operated by the user. However, this could be automated.

Preferably, a cover 53 is associated with the lever 51. The cover 53 is spaced away from the base when the supply block is in the first, open position (FIG. 1) and is spaced closer to the base when the supply block is in the second, closed position (FIG. 2), so as to shield the proximal end of the syringe when it is engaged by the air supply block 18.

Figure 10:
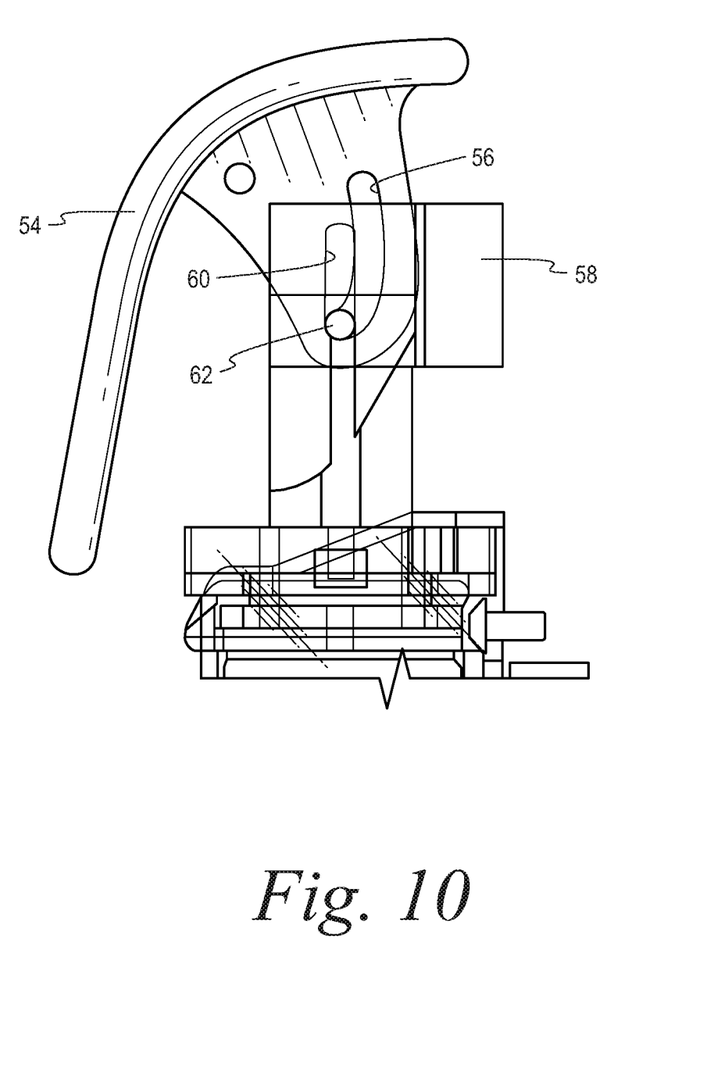
FIG. 10 is an enlarged fragmentary view of an alternate embodiment for an over-center latching assembly for moving the pneumatic driver into and out of sealing engagement with an associated disposable syringe.

Alternatively, and with reference to FIG. 10, a latch 54 may be provided for moving the air supply block 18 between the first and second positions. The latch 54 is pivotally mounted relative to the base 44 and comprises an arcuate track 56. A guide block 58 is secured to the base 44 that comprises a linear track 60 that is generally aligned with the longitudinal axis of the supply block 18. The air supply block 18 further includes a follower 62 received in both the arcuate track 56 of the latch 54 and the linear track 60 of the guide block 58, such that when the latch 54 is pivoted, the arcuate track engages 56 the follower 62 to move the follower 62 along the linear track 60, and thus move the air supply block 18 between the first and second positions. Preferably, the arcuate and linear tracks 56, 60 are in the form of slots in the latch and mounting block 54, 58, respectively, while the follower 62 is a pin forming part of the air supply block 18.

In order to maintain the air supply block 18 and lever/cover 50 in the open position to facilitate the loading of a syringe onto the support, the pneumatic driver 10 further comprises a first permanent magnet 64 secured to the base 44 and a second permanent magnet 66 secured to the air supply block 18. Preferably, the first magnet 64 is secured to the adapter plate 44a, so that its position is adjustable. When the air supply block 18 and lever/cover 50 are in the open position, the first and second magnets 64, 66 are in sufficiently close proximity so that the force of attraction between the magnets maintains the air supply block 18 in the open position in the absence of a further external force being applied to the air supply block 18 through the lever/cover 50. The magnets 64, 66 also provide for tactile feedback of the cover being in the open position.

Turning to the disposable syringe 12 that is part of the system, as described above, the syringe 12 comprises a barrel 14 with the cap 22 having a through-bore 24 secured to the proximal end of the barrel 14. In keeping with the application, and with reference to FIG. 11, the syringe 12 further includes a filter 68 secured to the cap 22 interior of the barrel 14 that covers the opening in the through bore 24 that communicates with the interior of the barrel. The filter 68 is such that air is considered to be sterile after passing through the filter.

More specifically, the filter 68 is a transducer protector that internally contains a hydrophobic and haemophobic membrane with a 0.2 micron pore section. Filters with this size of membrane pore are considered to be sterility filters and deliver air that is free of microbes above the 0.2 micron size. An exemplary filter is available from GVS S.p.A. of Rome, Italy, as product number TP100ACOG002AA00.

The filter 68 contains a port 70. The port 70 may be chemically bonded to the cap 22 using a solvent, such as cyclohexanone. Alternatively, the port 70 may be secured to the cap by means of screw threads, glue, ultrasonic bonding, or snap fit. In a further alternative, the cap 22 may also be configured to receive the filter membrane 68, thus eliminating the separate housing port 70.

The filter membrane 68 could be breached if the flow rate or air pressure rating is exceeded. Thus, the cap 22 and integrated filter 68 are preferably configured to allow removal of the cap 22, thus permitting evaluation of the filter 68 with a test apparatus to confirm that its integrity was maintained during use. A removable cap would also permit direct access to the stopper 20 so that a removable handle could be manually attached thereto to move the stopper in the event of a failure of the driver 10. In the illustrated embodiment, the port 70 for the filter 68 is configured to form a threaded luer lock 72 such that, upon removal of the cap 22 from the syringe 12, a filter integrity tester may be attached to the luer lock 72 to check the integrity of the filter 68.

Figure 12:
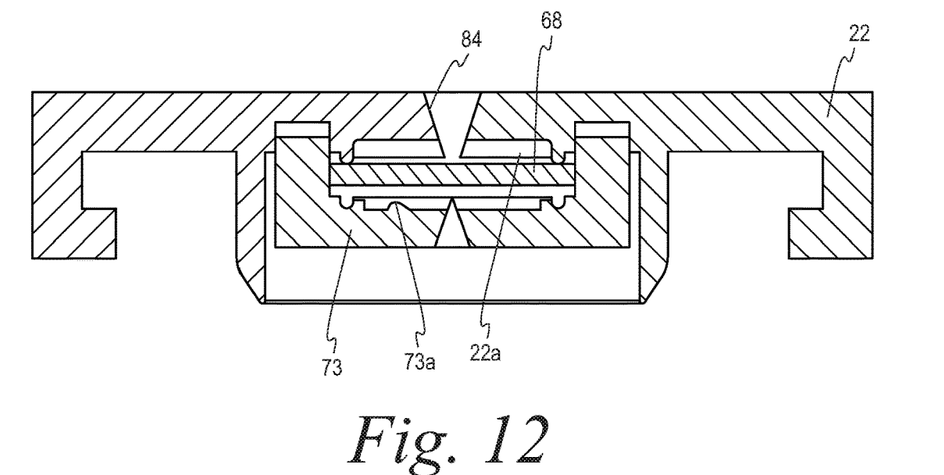
FIG. 12 is a cross-sectional view of an alternative embodiment of the assembly of the syringe cap and filter.
Figure 13:
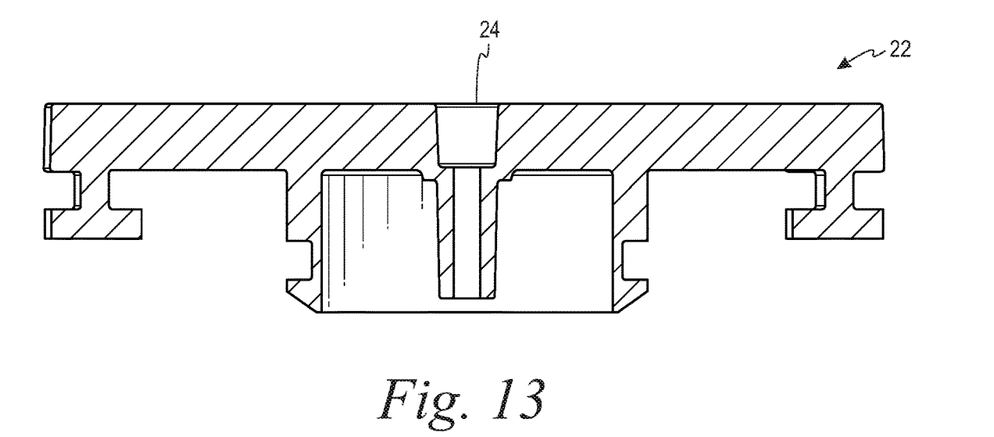
FIG. 13 is an enlarged cross-sectional view of further alternative configuration of the syringe cap.

With reference to FIG. 12, and alternate configuration for the assembly of the syringe cap 22 and filter 68 is shown in which the filter 68 is secured to the syringe cap by means of a retainer 73, with the assembly being secured together by, e.g., ultrasonic shear welding. The syringe cap 22 and retainer 73 may be provided with ribs 22a, 73a, respectively, for supporting the filter 68.

Figure 14:
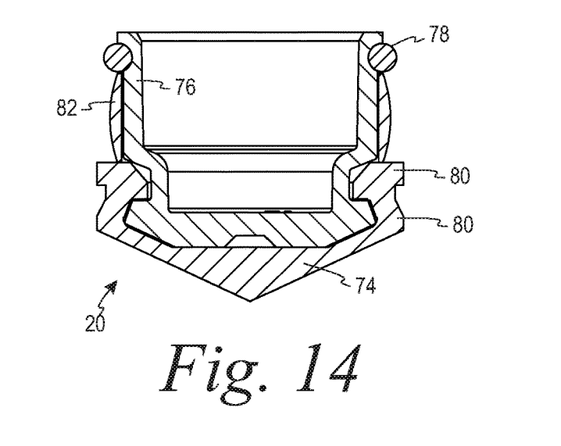
FIG. 14 is a cross sectional view of the stopper received in the barrel of the syringe.

A stopper, generally designated 20, is slidably received in the barrel 14 for movement within the barrel 14 between the first/proximal and second/distal ends of the barrel. As best seen in FIG. 14, the stopper 20 comprises a plunger head 74 mounted to a piston 76. As illustrated, the piston 76 has a hollow interior sized to receive the luer lock 72 of the port 70, thus providing for a maximum volume of the filled syringe when the stopper 20 is in the fully retracted position. The piston 76 is provided with a gasket or O-ring 78 that engages the interior wall of the barrel 14 that helps to keep the piston 76 aligned with the longitudinal axis of the syringe. The plunger head 74 is provided with outer edges 80 for sealingly engages the interior wall of the barrel 14.

Optionally, the stopper may include a reflective band 82 to provide for an enhanced IR return signal used for positioning the stopper within the syringe. The shape of the curvature of the reflective band 82 may be selected to optimize the reflective signal provided by the band 82 to the sensing elements. Alternatively, the material from which the piston is made may include reflective pigment additives for this same purpose.

In the event that the pneumatic driver is unavailable, the syringe 12 as described above may be actuated manually without breaking sterility. For example, a user can draw non-sterile air into a traditional syringe with a luer fitting, attach it to the cap, and push the plunger on the traditional syringe to drive the stopper in the sterile syringe. Any source of pressurized air could similarly be attached to the cap of the sterile syringe to drive the stopper without breaking sterility. Preferably, the inlet to the through bore on the top of the cap is configured to receive the tip of a standard syringe.

As illustrated, the through bore 24 terminates in a conical portion 84 that is of the same draft angle as ISO 594-1 and 594-2 male and female luer sections. This permits the nozzle tip of a syringe to friction fit inside the conical portion 84 to allow the air in the syringe to drive the stopper 72 in the event of a power failure, thus permitting the recovery of cells trapped in the syringe 12. Alternatively, the cap 22 may be formed with a luer lock that extends exterior of the barrel of the syringe and defines the inlet to the through bore 24, thus allowing for other pneumatic systems to be connected without breaching the sterility established by the filter 68.

Thus, an improved pneumatic driver and associated syringe have been disclosed. The description provided above is intended for illustrative purposes, and is not intended to limit the scope of the disclosure to any particular method, system, apparatus or device described herein.

The invention claimed is:

1. An actuator for a syringe, the syringe comprising an elongated barrel having a first end, and a cap secured to the first end having a through-bore, the actuator comprising:
   a) a source of pressurized air;
   b) a support for receiving and locating the syringe having the cap with the through-bore secured to the first end of the syringe; and
   c) a supply block configured to receive pressurized air from the source and having an outlet for delivery of pressurized air, the supply block being movable between a first position spaced apart from the cap of the syringe and a second position in contact with the cap with fluid communication being established between the outlet of the supply block and the through-bore in the cap;
   further comprising a base, wherein the source of pressurized air, the support for receiving the syringe, and the supply block are mounted to the base; and
   wherein the source of pressurized air and the support for receiving the syringe are affixed to the base and the supply block is movably attached to the base for movement between the first and second positions by a plurality of links, each link having a first and second end, the first end of each link being pivotally secured relative to the base and the second end of each link being pivotally secured to the supply block.

2. The actuator of claim 1 further comprising a seal associated with one of the outlet of the supply block or the through-bore in the cap to provide a seal between the outlet of the supply block and the through-bore in the cap when the supply block is in the second position.

3. The actuator of claim 1 further comprising a lever pivotally attached relative to the base and a further link having first and second ends, the first end of the further link being pivotally secured to the lever and the second end of the further link being pivotally secured to the supply block such that movement of the lever relative to the base moves the supply block between the first and second positions.

4. The actuator of claim 3 wherein the lever further comprises a cover, the cover being spaced away from the base when the supply block is in the first position and is spaced closer to the base when the supply block is in the second position.

5. The actuator of claim 1 further wherein the plurality of links comprises two pairs of links pivotally secured to the supply block and the base so that the links of each pair are substantially parallel throughout a range of motion from the first position to the second position.

6. The actuator of claim 1 further comprising a first permanent magnet secured to the base and a second permanent magnet secured to the supply block such that the first and second magnets are in proximity when the supply block is in the first position with a sufficient force of attraction to maintain the supply block in the first position in the absence of a further external force being applied to the supply block.

7. The actuator of claim 3 further comprising a first permanent magnet secured to the base and a second permanent magnet secured to the supply block such that the first and second magnets are in proximity when the supply block is in the first position with a sufficient force of attraction to maintain the supply block in the first position in the absence of a further external force being applied to the supply block.

8. The actuator of claim 4 further comprising a first permanent magnet secured to the base and a second permanent magnet secured to the supply block such that the first and second magnets are in proximity when the supply block is in the first position with a sufficient force of attraction to maintain the supply block in the first position in the absence of a further external force being applied to the supply block.

9. The actuator of claim 1 further comprising an air flow pathway from the source of pressurized air to the supply block, one or more valves for controlling air flow through the air flow pathway, one or more pressure sensors for measuring air pressure within the air flow pathway and providing a signal indicative of the air pressure, and a programmable controller configured to automatically control the air flow through the air flow pathway by actuation of the one or more valves in response to signals received from the one or more sensors.

10. The actuator of claim 2 further comprising an air flow pathway from the source of pressurized air to the supply block, one or more valves for controlling air flow through the air flow pathway, one or more pressure sensors for measuring air pressure within the air flow pathway and providing a signal indicative of the air pressure, and a programmable controller configured to automatically control the air flow through the air flow pathway by actuation of the one or more valves in response to signals received from the one or more sensors.

11. The actuator of claim 3 further comprising an air flow pathway from the source of pressurized air to the supply block, one or more valves for controlling air flow through the air flow pathway, one or more pressure sensors for measuring air pressure within the air flow pathway and providing a signal indicative of the air pressure, and a programmable controller configured to automatically control the air flow through the air flow pathway by actuation of the one or more valves in response to signals received from the one or more sensors.

12. The actuator of claim 4 further comprising an air flow pathway from the source of pressurized air to the supply block, one or more valves for controlling air flow through the air flow pathway, one or more pressure sensors for measuring air pressure within the air flow pathway and providing a signal indicative of the air pressure, and a programmable controller configured to automatically control the air flow through the air flow pathway by actuation of the one or more valves in response to signals received from the one or more sensors.

13. The actuator of claim 1 wherein the supply block defines a longitudinal axis generally aligned with a longitudinal axis of the syringe received in the support and the actuator further comprising a latch pivotally mounted relative to the base comprising an arcuate track, a guide block secured to the base comprising a linear track generally aligned with the longitudinal axis of the supply block, and the supply block further comprising a follower received in both the arcuate track of the latch and the linear track of the guide block, such that when the latch is pivoted, the arcuate track engages the follower to move the follower along the linear track and to thus move the supply block between the first and second positions.

14. The actuator of claim 1 wherein the outlet of the supply block comprises a luer fitting.

15. The actuator of claim 14 wherein the luer fitting is threaded and the supply block is rotatable.

16. An actuator for a syringe, the syringe comprising an elongated barrel having a first end, and a cap secured to the first end having a through-bore, the actuator comprising:
   a) a source of pressurized air;
   b) a support for receiving and locating the syringe having the cap with the through-bore secured to the first end of the syringe; and c) a supply block configured to receive pressurized air from the source and having an outlet for delivery of pressurized air, the supply block being movable between a first position spaced apart from the cap of the syringe and a second position in contact with the cap with fluid communication being established between the outlet of the supply block and the through-bore in the cap;

further comprising a base, wherein the source of pressurized air, the support for receiving the syringe, and the supply block are mounted to the base; and further comprising a first permanent magnet secured to the base and a second permanent magnet secured to the supply block such that the first and second magnets are in proximity when the supply block is in the first position with a sufficient force of attraction to maintain the supply block in the first position in the absence of a further external force being applied to the supply block.

\* \* \* \* \*